United States Patent
Stadthagen et al.

(10) Patent No.: US 11,511,273 B2
(45) Date of Patent: Nov. 29, 2022

(54) DRUG DETECTION VIA SURFACE ENHANCED RAMAN SPECTROSCOPY

(71) Applicant: SECURETEC DETEKTIONS-SYSTEME AG, Neubiberg (DE)

(72) Inventors: Torsten Stadthagen, Munich (DE); Markus Fremmer, Munich (DE)

(73) Assignee: SECURETEC DETEKTIONS-SYSTEME AG, Neubiberg (DE)

( * ) Notice: Subject to any disclaimer, the term of this patent is extended or adjusted under 35 U.S.C. 154(b) by 632 days.

(21) Appl. No.: 16/465,946

(22) PCT Filed: Dec. 4, 2017

(86) PCT No.: PCT/EP2017/081331
§ 371 (c)(1),
(2) Date: May 31, 2019

(87) PCT Pub. No.: WO2018/100202
PCT Pub. Date: Jun. 7, 2018

(65) Prior Publication Data
US 2020/0061604 A1    Feb. 27, 2020

(30) Foreign Application Priority Data
Dec. 2, 2016   (EP) .................... 16201916

(51) Int. Cl.
*B01L 3/00* (2006.01)
*G01N 21/65* (2006.01)
(Continued)

(52) U.S. Cl.
CPC ........ *B01L 3/5027* (2013.01); *A61B 10/0051* (2013.01); *G01J 3/44* (2013.01);
(Continued)

(58) Field of Classification Search
CPC ........... B01L 3/5027; B01L 2400/0406; B01L 2200/16; B01L 2300/028; A61B 10/0051;
(Continued)

(56) References Cited

U.S. PATENT DOCUMENTS 5,118,609 A     6/1992  Baier et al.
2009/0168052 A1*  7/2009  Burrell .................. G01N 21/65
                                                    356/73

FOREIGN PATENT DOCUMENTS

DE    3802366 A1   8/1989
EP    0699906 A2   3/1996
(Continued)

OTHER PUBLICATIONS

Yun Han et al: "Towards Full-Length Accumulative Surface-Enhanced Raman Scattering-Active Photonic Crystal Fibers", Advanced Materials, vol. 22, No. 24, May 3, 2010 (May 3, 2010), pp. 2647-2651. (Year: 2010).*
(Continued)

*Primary Examiner* — Dennis White
(74) *Attorney, Agent, or Firm* — McCoy Russell LLP

(57) ABSTRACT

The present invention relates to a method for determining an analyte using surface enhanced RAMAN spectroscopy and to a device which is suitable for this purpose.

20 Claims, 13 Drawing Sheets

Figure 1:
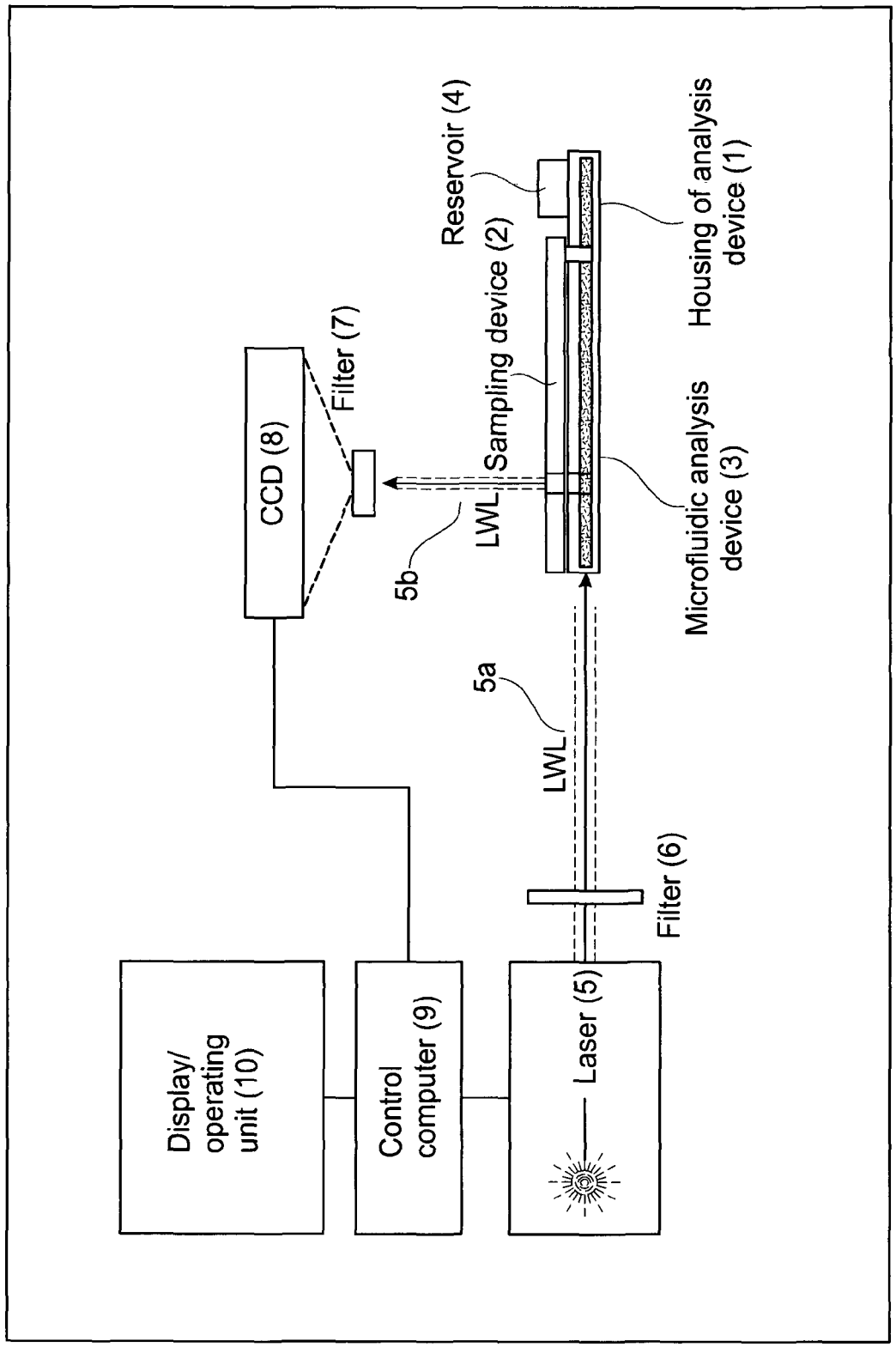

(51) Int. Cl.
*G01N 33/487* (2006.01)
*G01N 1/02* (2006.01)
*A61B 10/00* (2006.01)
*G01J 3/44* (2006.01)

(52) U.S. Cl.
CPC ..... *G01N 21/658* (2013.01); *G01N 33/48714* (2013.01); *A61B 2010/0009* (2013.01); *G01N 2001/028* (2013.01); *G01N 2201/0221* (2013.01)

(58) Field of Classification Search
CPC ........ A61B 2010/0009; A61B 10/0064; A61B 10/007; A61B 10/0045; G01J 3/44; G01N 21/658; G01N 33/48714; G01N 2001/028; G01N 2201/0221; G01N 2001/002
See application file for complete search history.

(56) References Cited

FOREIGN PATENT DOCUMENTS

| | | |
|---|---|---|
| EP | 2381258 A1 | 10/2011 |
| WO | 2004086979 A1 | 10/2004 |
| WO | 2007092173 A2 | 8/2007 |
| WO | 2009123911 A2 | 10/2009 |
| WO | WO-2011134946 A1 * | 11/2011 ........ B01L 3/502715 |

OTHER PUBLICATIONS

Han, Y. et al., "Towards Full-Length Accumulative Surface-Enhanced Raman Scattering-Active Photonic Crystal Fibers," Advanced Materials, vol. 22, No. 24, Jun. 28, 2010, 5 pages.

ISA European Patent Office, International Search Repod Issued in Application No. PCT/EP2017/081331, dated Mar. 9, 2018, WIPO, 3 pages.

European Patent Office, Office Action Issued in Application No. 17816604.7, dated Jan. 7, 2022, Germany, 6 pages.

* cited by examiner

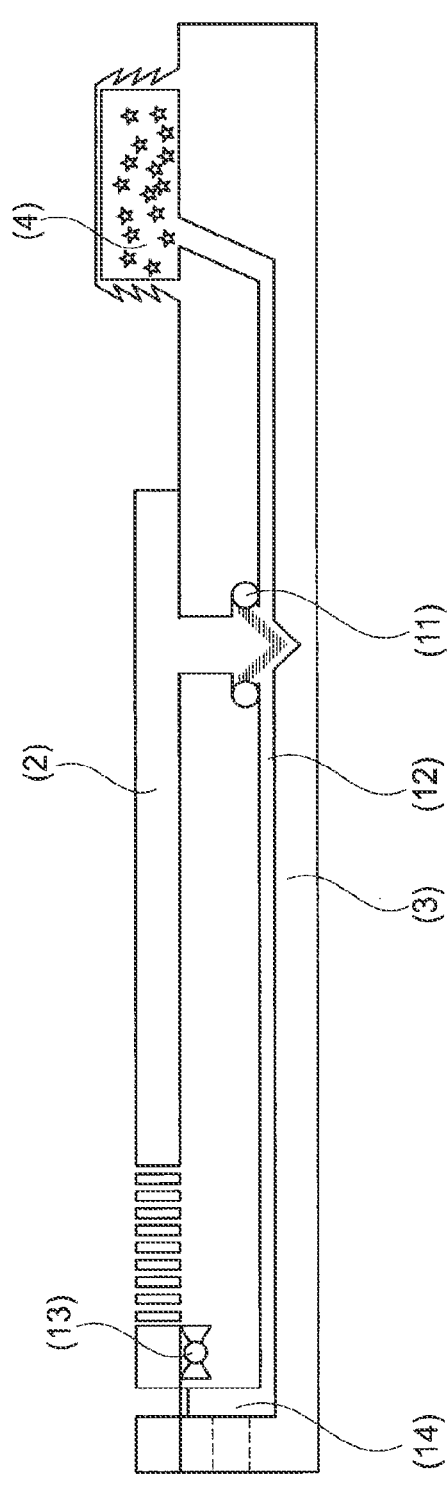
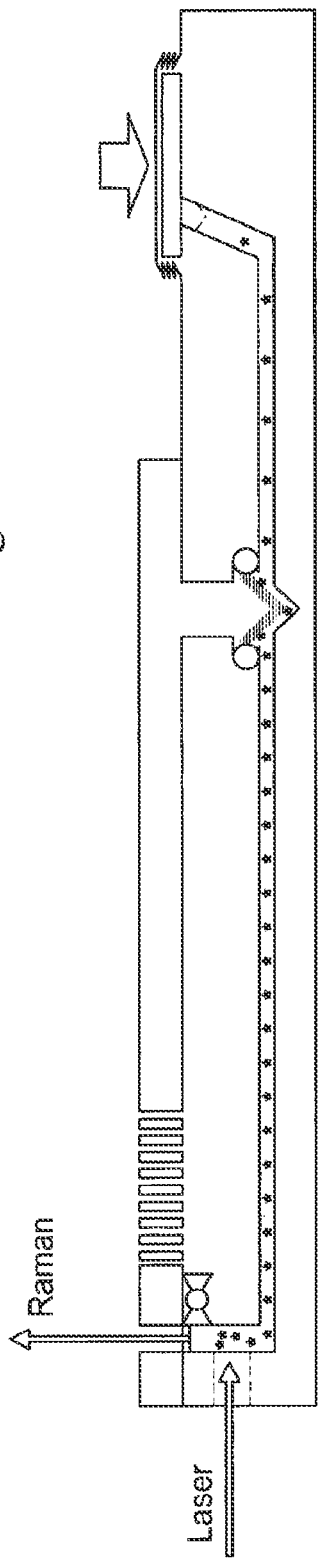
Fig. 2A
Fig. 2B

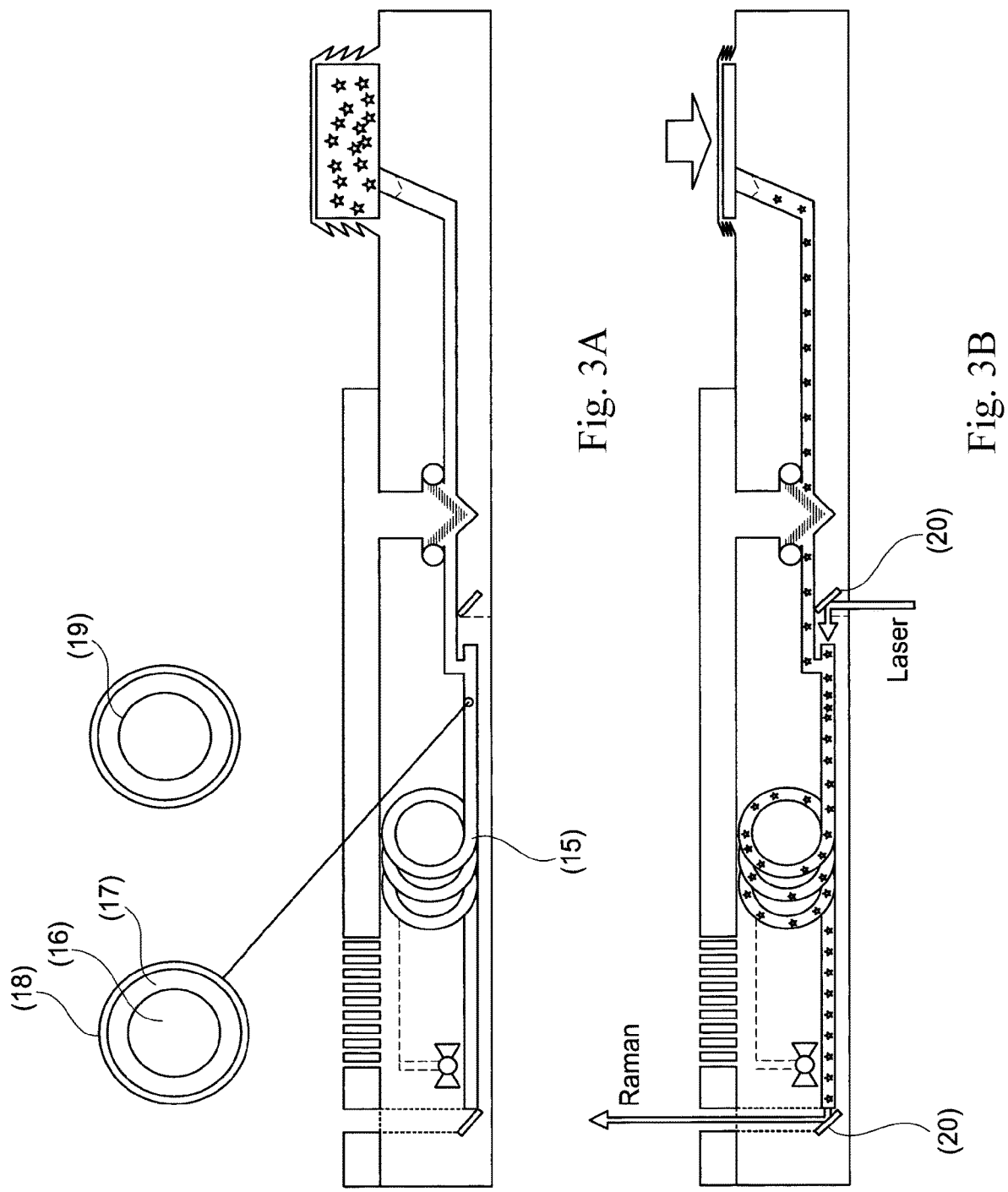

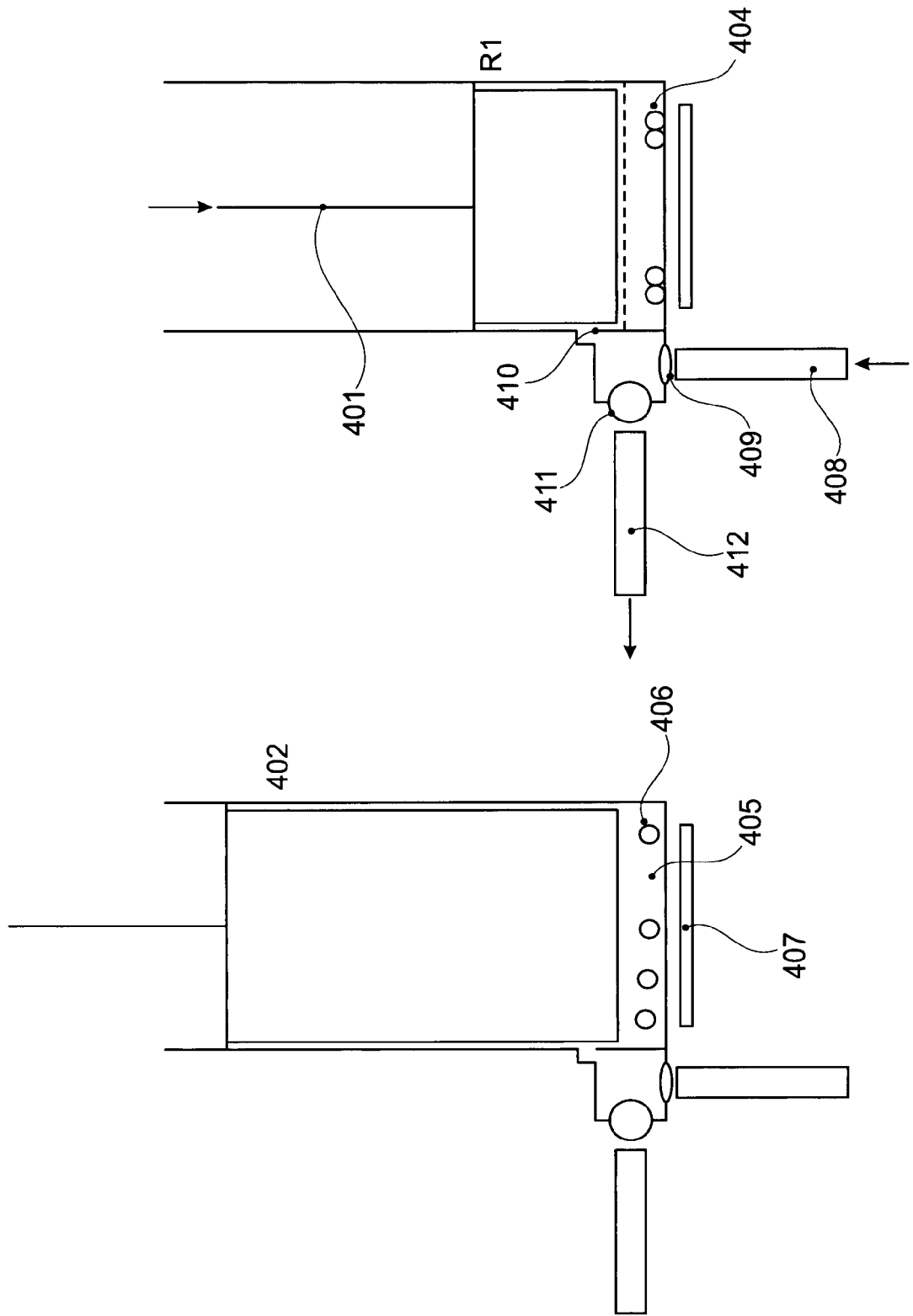

DRUG DETECTION VIA SURFACE ENHANCED RAMAN SPECTROSCOPY

CROSS-REFERENCE TO RELATED APPLICATION

The present application is a U.S. National Phase of International Patent Application Serial No. PCT/EP2017/081331 entitled "DRUG DETECTION VIA SURFACE ENHANCED RAMAN SPECTROSCOPY," filed on Dec. 4, 2017. International Patent Application Serial No. PCT/EP2017/081331 claims priority to European Patent Application No. 16201916.0 filed on Dec. 2, 2016. The entire contents of each of the above-referenced applications are hereby incorporated by reference for all purposes.

TECHNICAL FIELD

The present invention relates to a method for determining an analyte and to a device which is suitable for this purpose.

BACKGROUND AND SUMMARY

The ability to detect and identify trace amounts of chemicals has become increasingly important in a wide variety of scientific disciplines such as in the field of medicinal-, environmental-, food- and agroanalytics. A particular field of application of analytical techniques that is important in practice is detecting drugs in bodily fluids or on surfaces which are contaminated with drugs. The number of drug related emergency room visits has drastically increased in recent years including cases attributed to illicit drugs and pharmaceutical drugs. Illicit drugs include cannabis, cocaine, heroin, methamphetamines, PCP, MDMA (known as ecstasy), and LSD. Pharmaceutical drugs include prescription and over-the-counter drugs, the leading prescription drugs being oxycodone, hydrocodone, and diazepam.

Drug consumption is a large problem in nearly all societies. Consumers not only harm themselves but also others, for example, when driving a motor vehicle under the influence of drugs. In order to decrease the risk of danger to others, it is necessary to have effective ways of measuring drug consumption on location, for example at a roadside inspection.

An aspect of major importance especially for detecting drugs is the specificity, sensitivity, and rapidity of the tests which are used. Usually, it is not known which drug a person consumed as there is a wide variety of different illicit and pharmaceutical drugs. It is thus necessary to have a test that can recognize as many different analytes as possible. On the one hand there is a need for highly sensitive detection methods so as to be able to trace the presence of drugs reliably and rapidly even with small sample volumes or when using complex sample material such as saliva. On the other hand, the test formats should also have a high specificity to the substance which is to be traced in each case so as to exclude false-positive measurement results, and thus provide authoritative information as to which specific drug the tested substance is. Ideally, the device would be portable, easy to use, and relatively non-invasive. The last requirement can best be met using saliva as the sample medium.

Many different types of screening devices are available in the art such as immunoassay kits that provide drug identification. The main problem with immunological tests, however, is that they are only suitable for a limited number of analytes. They usually contain detecting reagents for the most common drugs. However, it is not possible to cover a wide range of drugs.

Another method of drug detection is based on spectroscopic measuring. In a lab, sophisticated instruments such as gas chromatographs coupled with mass spectrometers can be used to verify drug identification as well as provide quantification. However, such instruments are not transportable and cannot be used for drug detection on location.

In recent years, the potential of surface enhanced Raman spectroscopy (SERS) to both identify and quantify drugs and their metabolites was investigated. This approach is based on the extreme sensitivity of SERS demonstrated by the detection of single molecules, the ability to measure very small samples, and the ability to identify molecular structures of drugs through the rich vibrational information provided by Raman spectroscopy. A further advantage of this detection method is the ease of adding a new detectable analyte by adding its spectral "fingerprint" to the spectral library. In order to allow for drug detection on location, portable Raman spectrometers are needed.

Based on the above-described test systems, the object of the present invention was to provide a method for determining a wide variety of analytes, particularly for determining drugs, in which method the drawbacks of the prior art are at least partially overcome. In particular, the method should have a high sensitivity and specificity to a wide variety of analytes, be simple to implement, and make a rapid determination.

This object is achieved according to the invention by a method for detecting an analyte in a sample comprising steps:

(a) receiving a sample containing an analyte by means of a sampling device comprising a sample matrix and optionally an eluent for eluting the analyte from the sample matrix, (b) introducing the sampling device into an analysis device comprising at least a first and a second region, wherein the first region is configured for introducing the sampling device and the second region is configured for detecting the analyte, (c) transferring the analyte from the first region to the second region of the analysis device, and (d) determining the presence or/and amount of the analyte in the second region by means of surface enhanced Raman spectroscopy (SERS).

Surprisingly, in the context of the present invention, it has been found that by means of the method according to the invention, analytes can be detected in a simple and reproducible manner with a high sensitivity and specificity and without requiring large amounts of the analyte-containing sample.

The method according to the invention requires the provision of an analysis device which is suitable for determining the analyte and which comprises at least a first and a second region. The first region of the analysis device is configured for introducing a sampling device by means of which a sample of the analyte was taken in advance, whilst the second region is configured for detecting the analyte via surface enhanced Raman spectroscopy. For transferring the analyte from the first region to the second region of the analysis device, the two regions have to be in fluid communication. Preferably, the transfer of the analyte from the first to the second region of the analysis device is initiated by an implementation step which is to be carried out by the user.

The term "in fluid communication", as used in the context of the present application, means that the respective regions of the analysis device are connected such that a fluid can be transferred from one region to the other. For example, the regions can be interconnected by microfluidic structures such as microchannels, stages, branches or/and chambers, that make it possible to transfer or process fluids within the analysis device. Microfluidic structures such as those mentioned above can be manufactured by methods known to a person skilled in the art, such as roll-to-roll printing or injection moulding using suitable materials in particular plastic material, according to the respective demands of the analysis device.

In the method according to the invention, a sample which shall be examined for the presence and/or amount of an analyte is received from a subject by means of a suitable sampling device. For example, a saliva sample can be readily obtained by swabbing the buccal epithelial tissues in the donor's mouth, or through placing a sampling element in the subject's mouth for a certain period of time to allow for the absorption of saliva thereon. In principle, as a sampling device any element can be used, which is capable of receiving a sample of the analyte and releasing it virtually quantitatively upon subsequent contact with an eluent and/or mechanical deformation, that is to say at an amount of at least 95% by weight based on the total weight of the received sample. Sampling elements which are particularly suitable for the purposes of the present invention are disclosed for example in EP 1 608 268 A1 and WO 2004/086979 A1, the disclosure of which is hereby incorporated by reference.

The sampling device comprises a sample matrix which is configured for receiving the sample. The sample matrix may in principle consist of any material which appears useful to a person skilled in the art for the purposes of the present invention, and which makes it possible both to accumulate the analyte on the sampling element and subsequently release it e.g. upon bringing it into contact with an eluent and/or upon mechanical compression such as by squeezing or other otherwise deforming it. Thus, as well as the sampling devices disclosed in EP 1 608 268 A1 and WO 2004/086979 A1, sampling devices, which comprise a sample matrix made of absorbent materials, in particular fabrics, non-wovens or/and porous matrices (for example membranes and sponges) may also be considered. Suitable non-wovens are disclosed for example in DE 38 02 366 A1 and EP 0 699 906 A2, the disclosure of which is hereby explicitly incorporated by reference.

So as to provide high sensitivity and specificity when determining the analyte, the surface of the sample matrix may be chemically pretreated before being used for the first time; in this way, it is possible to improve the receipt of the analyte during sampling or/and to minimize adhesion of the analyte to the sampling element. Thus, according to a preferred embodiment, the method according to the invention provides that the sampling element comprises a transfer reagent containing at least one protein, at least one carbohydrate, at least one sugar alcohol or/and at least one salt, in particular an inorganic salt. However, it is understood that the sampling element is also functional without a transfer reagent. Therefore, in another embodiment, the method according to the invention provides that the sampling element does not comprise a transfer reagent.

A transfer reagent which promotes the transfer of the analyte from the sample surface to the sample matrix or/and the subsequent release of the analyte, in particular by blocking free binding sites on the sample matrix or/and influencing the analyte properties, can for example be impregnated on the sample matrix for this purpose. Techniques which may be used for applying the transfer reagent to the sample matrix are generally known to a person skilled in the art.

The term "carbohydrate", as used in the present application, refers to monosaccharides, oligosaccharides and polysaccharides of the general empirical formula $C_nH_{2n}O_n$, which may each be of natural or synthetic origin. In the context of the invention, monosaccharides or oligosaccharides are preferably used, in particular naturally occurring tetroses, pentoses and hexoses, such as erythrose, threose, ribose, arabinose, lyxose, xylose, allose, altrose, galactose, glucose, gulose, idose, mannose, talose and fructose, which may each be present in the D form or in the L form, being used as monosaccharides. In particular naturally occurring disaccharides and trisaccharides, such as lactose, maltose, saccharose, trehalose, gentianose, kestose and raffinose, may be used as oligosaccharides. In a particularly preferred embodiment of the invention, the transfer reagent comprises a carbohydrate selected from the group consisting of glucose, lactose, maltose and saccharose.

The term "sugar alcohol", as used in the present application, refers to monosaccharide sugar alcohols of the general empirical formula $C_nH_{2n+2}O_n$ and disaccharide alcohols of the general empirical formula $C_nH_{2n}O_{n-1}$, which may in each case be of natural or synthetic origin.

Preferred monosaccharide sugar alcohols include glycerol, erythritol, threitol, ribitol, arabinitol, xylitol, allitol, altritol, galactitol, glucitol, iditol and mannitol, which may each be present in the D form or in the L form. In particular isomalt, lactitol and maltitol may be used as disaccharide sugar alcohols. In a particularly preferred embodiment of the invention, the transfer reagent contains a sugar alcohol selected from the group consisting of glucitol, glycerol, mannitol and xylitol.

In the context of the method according to the invention, a transfer reagent is preferably used, which comprises (a) at least one protein selected from the group consisting of gelatin, ovalbumin and bovine serum albumin, (b) skimmed milk powder, (c) at least one carbohydrate selected from the group consisting of glucose, lactose, maltose and saccharose, (d) at least one sugar alcohol selected from the group consisting of glucitol, glycerol, mannitol and xylitol, or/and (e) at least one salt selected from the group consisting of calcium chloride, potassium chloride, magnesium chloride, sodium chloride and a borate.

Particularly preferably, the transfer reagent which may be used according to the invention comprises at least one protein selected from the group consisting of gelatin, ovalbumin and bovine serum albumin, or/and skimmed milk powder.

The concentration of the at least one protein, at least one carbohydrate, at least one sugar alcohol or/and at least one salt in the above-described transfer reagent may be adapted by a person skilled in the art, according to the respective demands on the analyte, but is usually approximately 0.01 to approximately 15% by weight based on the total weight of the transfer reagent. If the transfer reagent comprises salts, they are usually added in concentrations of approximately 1 µM to approximately 1 M.

In addition to the at least one protein, at least one carbohydrate, at least one sugar alcohol or/and at least one salt, the transfer reagent may optionally comprise further reagents which promote a transfer of the analyte from the surface which is to be analysed to the sample matrix or/and the subsequent release of the analyte onto the eluent, such as a detergent or/and an organic solvent. Examples of detergents include, among others, cholamidopropane sulphonate, octyl glucoside, polidocanol, polyalkylene glycol ether (for example Brij®, Synperonic®) and polysorbates (for example Tween® 20, Tween® 80), which are conventionally used in concentrations of approximately 0.01 to approximately 5% by weight based on the total weight of the transfer reagent. Examples of organic solvents include in particular dimethyl sulphoxide, ethanol, methanol, glycerine and mixtures thereof, which are added to the transfer reagent in a concentration of usually <30% by weight.

In a preferred variant, the method according to the invention provides the use of a sampling device which comprises a volume indicator. During sampling, the volume indicator displays to the user whether a sufficient, defined sample volume for determining the analyte has been taken. This is of decisive importance in particular when sampling fluids such as saliva since in general an optimum performance of the respective test system can only be provided if a defined sample volume is provided. A negative influence on the test system by the test subject, for example by the subject depositing too low a sample volume, can be prevented by the volume indicator, and as a result the sensitivity, specificity and overall reliability of the test system can ultimately be optimised.

Particularly preferably, the volume indicator is a colour indicator which changes colour upon contact with a sufficient sample volume, for example upon contact with a sufficient volume of bodily fluid, and thus correlates with the sample volume required for determining the analyte.

Any colour indicator which is known to a person skilled in the art and appears suitable for the purposes of the present invention may be used as a colour indicator as long as it meets the above criteria and is also non-toxic. Examples of colour indicators of this type include in particular common pH colour indicators or plant dyes, which can be applied to the sampling element by vapour deposition, imprinting, spraying or/and soaking.

Release of the analyte from the sample matrix of the sampling device can be accomplished by means of an eluent and/or by mechanical compression. Preferably, the sample-matrix is flushed with an eluent and release of the analyte is additionally assisted by mechanical compression of the sample matrix such as by squeezing or otherwise deforming it.

According to the invention, releasing the analyte from the sample-matrix can be accomplished in the sampling device, preferably before introducing it into the analysis device, or it can be effected in the analysis device. In case the analyte is to be eluted in the sampling device, said sampling device comprises two parts, one that is configured to take up the sample of the analyte and comprises the sample matrix and one that comprises the eluent. It is understood that the two parts can be provided separately or as a combined tool. Alternatively, it is possible to release the analyte-containing sample from the sample matrix or to assist the release by mechanically deforming the sample matrix. For example, the part of the sampling device configured to take up the analyte-containing sample, i.e. the part including the sample matrix, can be introduced into an elution container and manually compressed therein. An exemplary two part sampling device is shown in FIG. 4.

In case the analyte is to be eluted from the sample matrix in the analysis device, the eluent can be provided in the sampling device or in the analysis device such that it comes into contact with the sample matrix only after the sampling device has been introduced into the analysis device. For example, the eluent can be stored in a separate region or compartment of the sampling device or the analysis device which is connected with the first region of the analysis device only upon introducing the sampling device. Further, it is possible to release the analyte-containing sample from the sample matrix or to assist the release by mechanically deforming the sample matrix. For example, after introducing the sampling device into the first region of the analysis device, the sample matrix can be squeezed or otherwise compressed, to release the analyte-containing sample.

In step (b) of the method according to the invention, the sampling device which comprises the sample of the analyte is introduced into the first region of the analysis device, which region is preferably in the form of a chamber. It is understood that not necessarily the sampling device as a whole has to be introduced but it is sufficient to introduce a portion of the sampling device such that the analyte can be transferred from the sampling device to the analysis device. In this context, the sampling device and the first region of the analysis device, which is configured for receiving or integrating the sampling device, are configured in such a way that the first region is tightly sealed after the sampling device is introduced and no fluid communication can take place between the interior of the first region and the external environment.

When introducing the sampling device into the first region of the analysis device, the sample matrix of the sampling device may be wetted with the analyte-containing sample. This embodiment is exemplified in FIGS. 2 and 3. Alternatively, the sampling device may comprise a solution of the analyte, e.g. the analyte-containing sample released from the sample matrix or a solution of the analyte or analyte-containing sample in an eluent. In the latter case, the analyte was previously eluted from the sample matrix by contacting it with an eluent.

Once a sampling device including a sample matrix that is wetted with the analyte-containing sample has been received in the first region of the analysis device, and it has been ensured that the first region is sealed off from the external environment; eluent can be introduced into the first region of the analysis device, to elute the analyte from the sampling device and distribute it preferably homogeneously in the eluent. Alternatively or additionally, the sample matrix can be compressed or otherwise mechanically deformed, to release the analyte-containing sample or to assist release. In a preferred embodiment of the invention, eluent is introduced into the first region and a homogeneous mixture of analyte and eluent is provided. This can be ensured for example by a microfluidic mixing path or another microfluidic mixing structure which is known to a person skilled in the art.

According to the invention, the eluent can be introduced into the first region of the analysis device in any desired manner. Thus, in a variant of the invention, the eluent can be stored in the sampling device which is used according to the invention. For this purpose, the sampling device may for example comprise an ampulla which contains the eluent, and which is opened and releases the eluent when the sampling device is introduced into the first region of the analysis device. Alternatively, the eluent can be stored in a separate region of the analysis device, which separate region is in fluid communication with the first region and from which the eluent can be flushed out into the first region of the analysis device, for example by way of an implementation step which is to be carried out separately by the user.

According to the embodiment of the invention wherein a release, in particular an elution takes place prior to the introduction of the sampling device into the analysis device, the sampling device can, for example, contain a part for taking up the sample including the sample matrix and an elution container including the eluent. Both the part for taking up the sample and the elution container can be disposable products. For eluting the analyte, the two parts are connected such that the eluent can come into contact with the sample whereas no fluid communication with the external environment is possible. For example, release of the eluent can be accomplished by way of an implementation step which is to be carried out by the user. The elution can be facilitated by manual shaking. Thus, in this variant, the invention provides that a homogeneous mixture of analyte and eluent is provided in the sampling device. It is also possible to release the sample from the sample matrix or to facilitate release by manual compression such as squeezing or otherwise deforming the sample matrix.

The sampling device comprising a solution of the analyte (in particular an analyte-containing sample released from the sample matrix or a solution of the analyte or analyte-containing sample in the eluent) is then introduced into the analysis device as described above. In case an elution of the analyte from the sample matrix has previously been carried out, a further elution in the analysis device is not necessary. It is possible, however, that additional eluent is introduced into the first region of the analysis device in order to produce a more homogenous mixture or to allow the mixture to be brought into contact with other components. In any case, it is ensured that after introducing the sampling device into the first region of the analysis device, the first region is sealed off from the external environment.

When a suitable combination of sampling device and eluent is used, it can be ensured by means of the above sequence of steps that the analyte is eluted from the sampling device substantially quantitatively, that is to say in an amount <95% by weight based on the total weight of the received sample, the analyte is released substantially quantitatively from the sample matrix, and the analyte and eluent are mixed completely. Quantitative release of the analyte from the sample matrix and from the sampling device are of essential importance for the maximum sensitivity of diagnostic test systems since bodily fluids which contain large amounts of proteins, lipids and carbohydrates, which in turn can lead to undesirable consequences in immunochemical reactions, are often used as samples, for example for detecting drugs.

In the context of the present invention, in principle any liquid which can release the analyte from the sample matrix can be used as the eluent. However, in the method disclosed herein, buffer solutions are preferably used which may optionally contain further reagents, in particular at least one protein, at least one carbohydrate, at least one sugar alcohol, at least one detergent or/and at least one organic solvent, in each case as disclosed above, in concentrations of usually approximately 0.05 to approximately 1.5% by weight. In the context of the method according to the invention, a preferably aqueous eluent which comprises 3-[(3-cholamidopropyl)dimethylammonio]-1-propane sulphonate as a component is considered to be particularly preferred. By way of a suitable combination of the above reagents, synergy effects can be achieved as a function of the structure of the respective analyte, and as a result the elution of the analyte from the sampling device or the release of the analyte from the sample matrix can be improved, and in this way the sensitivity or/and specificity of the analyte determination can be increased.

In step (c) of the method according to the invention, the analyte is transferred from the first to the second region of the analysis device. At this stage of the method, the analyte is present in a solution comprising at least the analyte (or the analyte-containing sample) and the eluent. This solution is herein also called an "eluate". The transfer can be initiated by an implementation step which is to be carried out by the user. Preferably, a defined volume of the eluate is transported into the second region. Accordingly, the second region should be configured to receive the eluate or a defined volume of the eluate. Further, it is preferred for the analysis device to be adapted to dissipate any gas or liquid previously present in the second region of the analysis device, that is displaced by the eluate entering the second region. The analysis device may for example comprise a region configured for absorbing excess liquid and/or a valve for allowing a balance of pressure. The transfer of the eluate from the first region into the second region can additionally be used to achieve an even higher level of homogeneous mixing of the sample and the eluent. This may preferably be achieved by way of a microfluidic mixing path or another microfluidic structure which is known to a person skilled in the art. According to this aspect of the invention, the analysis device may comprise a microfluidic structure.

The second region of the analysis device may in principle be configured in any form as long as it can receive the eluate which is transferred from the first region. In a preferred variant of the invention, the second region of the analysis device is in the form of a single chamber.

In the second region of the analysis device, the analyte is detected by means of surface enhanced Raman spectroscopy (SERS). In this context it is necessary for the analyte molecules to be associated with a SERS substrate such as SERS active particles. In the method according to the invention, the analyte molecules remain in solution and are in close vicinity to the SERS substrate, particularly the SERS active particles. In a specific embodiment, a solution of analyte molecules is present in the second region of the analysis device, wherein SERS active particles are suspended in the solution. Alternatively or additionally, SERS active particles can be immobilized in the second region of the analysis device, for example in the form of a coating on the inner surface of the second region of the analysis device.

According to the present invention, "SERS active particles" are preferably nanoparticles of a metal known to be SERS-active. For example, nanoparticles of silver, copper, or gold are suitable for use as SERS active particles in terms of the invention. Further, it is also possible to use nickel, palladium, or platinum nanoparticles as well as alloys of any of the above-mentioned metals. The metal type and particle size will normally be so selected as to match a given excitation wave length for optimizing the generation of surface plasmons and hence SER scattering. More than one species of metal nanoparticles can be used if desired. Metal alloys can be prepared (e.g. by under potential electrochemical deposition) to have optical constants appropriate to the generation of surface plasmons, and can also be used.

Contacting the solution of the analyte and SERS active particles can be accomplished at any point during their transport from the sample matrix to the second region of the analysis device. For example, it is possible to use an eluent containing SERS active particles, preferably nanoparticles. It is not crucial whether the SERS active particles are brought into contact with the analyte in the sampling device or only in the analysis device, provided that it is guaranteed that in the second region of the analysis device, analyte molecules are associated with the SERS substrate. In case both the sampling device and the analysis device contain an eluent, one or both of the eluents may contain SERS active particles. Preferably, SERS active nanoparticles are dispersed in at least one eluent. Then, during the elution of the analyte, the analyte is at the same time brought into contact with the SERS active particles. In the resulting mixture, the analyte is dissolved and the SERS active nanoparticles are dispersed. The transfer of the eluate from the first region to the second region of the analysis device enables a good mixing with the SERS active particles.

Alternatively or additionally, SERS active nanoparticles can also be supplied in the second region of the analysis device. For example, SERS active particles may be present in dried form in the second region and then be dispersed in the eluate once it is introduced into the second region.

According to a particularly preferred embodiment of the present invention, the second region of the analysis device comprises a hollow core optical fiber that may optionally be coated on its inside surfaces and that is configured to receive the analyte-containing sample in its hollow core. This embodiment is illustrated in FIG. 3A. Most preferably, the coating on the inside surface of the hollow core optical fiber contains SERS active nanoparticles. By this means, a further enhancement of the Raman effect can be achieved.

In step (d) of the method of the present invention, the presence and/or amount of analyte is determined by means of surface enhanced Raman spectroscopy. In order to do this, monochromatic excitation radiation is irradiated into the second region of the analysis device. In case analyte molecules are present in the second region, a specific Raman radiation is produced, which is detected and evaluated by a sensor. An apparatus for surface enhanced Raman spectroscopy according to the present invention may consist of the following principle components: a laser source to generate SER scattering in the sample, optics to direct the laser beam to the sample and collect the scattered radiation, a Raman spectrometer to separate the scattered light by wave length or frequency to form a Raman spectrum. The wave length of the monochromatic laser light will preferably be selected to match the optical constants of the metal particles, to thereby optimize the generation of a plasmon field. Pre-sample conditioning optics can be used to remove undesirable wave lengths of light, such as plasma lines. Optics for directing the excitation light beam toward the sample may employ, for example, a mirror, a prism, a fiber optic, an optical interference filter, or a notch filter, and further optics may be used to maximize the illumination of the sample, the distribution of radiant energy, and the collection of the scattered radiation. Such further optics may comprise, for example, a collimating lens, a cylindrical lens, a spherical lens, a combination of lenses, a bifurcated fiber optic, or a combination of excitation and collection fiber optics. Such optics can be used to collect radiation reversely along the optical axis of excitation (back-scattering), forwardly along the axis of excitation (forward-scattering), or at an angle to the axis of excitation (side-scattering). Post-sample conditioning optics are used to remove undesired radiation, principally, the elastically scattered (Rayleigh) radiation having a wave length of light identical to the incident radiation, using interference or notch filters. Finally, optics used to redirect the scattered radiation into the Raman instrument may comprise a mirror, a prism, or a fiber optic coupled with appropriate lenses to match the aperture of the Raman instrument. The Raman instrument separates and disperses the light into its component wave lengths using a prism or grating, or into its component frequencies using an interferometer. A detector of the instrument transforms the photon energy into electrical energy such as by use of a photomultiplier tube, photodiode, or a single or two-dimensional array of photodiodes. The electrical energy is then used to produce a Raman spectrum using means for displaying wave lengths on the X-axis (usually in units of wave numbers) and for displaying photon energy on the Y-axis (usually in arbitrary units). This can be accomplished using a plotter or computer with appropriate hardware and software.

For the detection of analytes, preferably a handheld Raman spectrometer is used comprising a laser light source for producing monochromatic radiation, optionally a laser reflection filter for blocking unwanted radiation, an imaging and filter unit, a sensor for detecting Raman radiation, a control computer, and a display/operating unit. The basic structure is shown in FIG. 1. Using an optical filter (see FIG. 1(6)), the laser radiation required for excitation of the scattered radiation can be optimized and using an optical fiber further directed to the measuring point and focused on the detection chamber. The response radiation produced by the solution is preferably coupled in a 90° scatter geometry into an optical fiber and thus directed to an optical imaging and filter unit (see FIG. 1(7)). The remaining Raman radiation can be focused on a CCD chip (see FIG. 1(8)). By using a subsequent control computer (FIG. 1(9)), the spectrometric evaluation can be performed by comparing the obtained spectrum ranges with the spectrum ranges on file.

The result of the measurement in step (d) is a qualitative positive/negative signal for the detected analytes. Additionally, the amount of analyte contained in the sample can be determined by the intensity of the measurement results.

Alternative configurations of the analysis device or the individual regions thereof will be apparent to a person skilled in the art on the basis of his general technical knowledge in combination with the above explanations.

The method according to the invention makes it possible to determine a wide variety of analytes with high sensitivity and specificity. Thus, according to the invention it is preferably possible to determine analytes with a specificity of at least 95% or/and a sensitivity of at least 90%.

More preferably, determination takes place with a specificity of at least 98% or/and a sensitivity of at least 95% in such a way that by the method disclosed herein, analytes can be detected down to a lower detection limit of approximately 1 ng/ml sample.

The method according to the invention can be used for determining any biological or chemical substance. Preferably, however, the method disclosed herein is used for tracing an analyte selected from the group consisting of amphetamines, methamphetamines, methadone, ketamines, cannabinoids, and synthetic cannabinoids, in particular $\Delta^9$-tetrahydrocannabinol, opiates, in particular morphine, codeine or dihydrocodeine, opioids, in particular heroin, tropane alkaloids, in particular cocaine, or benzodiazepines. $\Delta^9$-tetrahydrocannabinol and cocaine are particularly preferred as analytes.

The analyte may be from any desired source, such as the surface of an object which is wetted with the analyte or a bodily fluid, such as whole blood, plasma, serum, urine, saliva or sweat. Preferably, the presence or/and the amount of an analyte in a sample of saliva or sweat are determined by the method disclosed herein. The sample amount required for carrying out the method is usually approximately 0.1 µl to approximately 1000 µl or 1 µl to 500 µl, preferably approximately 5 µl to approximately 250 µl and most preferably approximately 30 µl to approximately 150 µl.

In a further aspect, the invention relates to a kit which is preferably used for carrying out the above-disclosed method and which comprises the following components:

(a) a sampling device configured for taking up a sample containing an analyte, wherein the sampling device comprises a sample matrix and optionally an eluent for eluting the analyte from the sample matrix and (b) an analysis device for determining the analyte, comprising (i) a first region which is configured for introducing the sampling device, (ii) optionally an eluent for eluting the analyte from the sampling device, (iii) a second region which is configured for detecting the presence and/or amount of the analyte by means of surface enhanced Raman spectroscopy, and (iv) optionally a housing, wherein at least one of the sampling device and the analysis device comprises an eluent and at least one of the sampling device and the analysis device comprises SERS active particles.

As regards preferred configurations of the analysis device, and of the sampling device which are contained in the above kit, reference is made to the statements made in connection with the description of the method according to the invention.

According to a preferred embodiment of the invention, the kit further comprises a radiation source (for generating monochromatic light, preferably laser radiation), a detector for detecting inelastically scattered radiation, and optics for directing radiation.

The invention will be described in greater detail by way of the following drawings and examples.

Figure 4A:
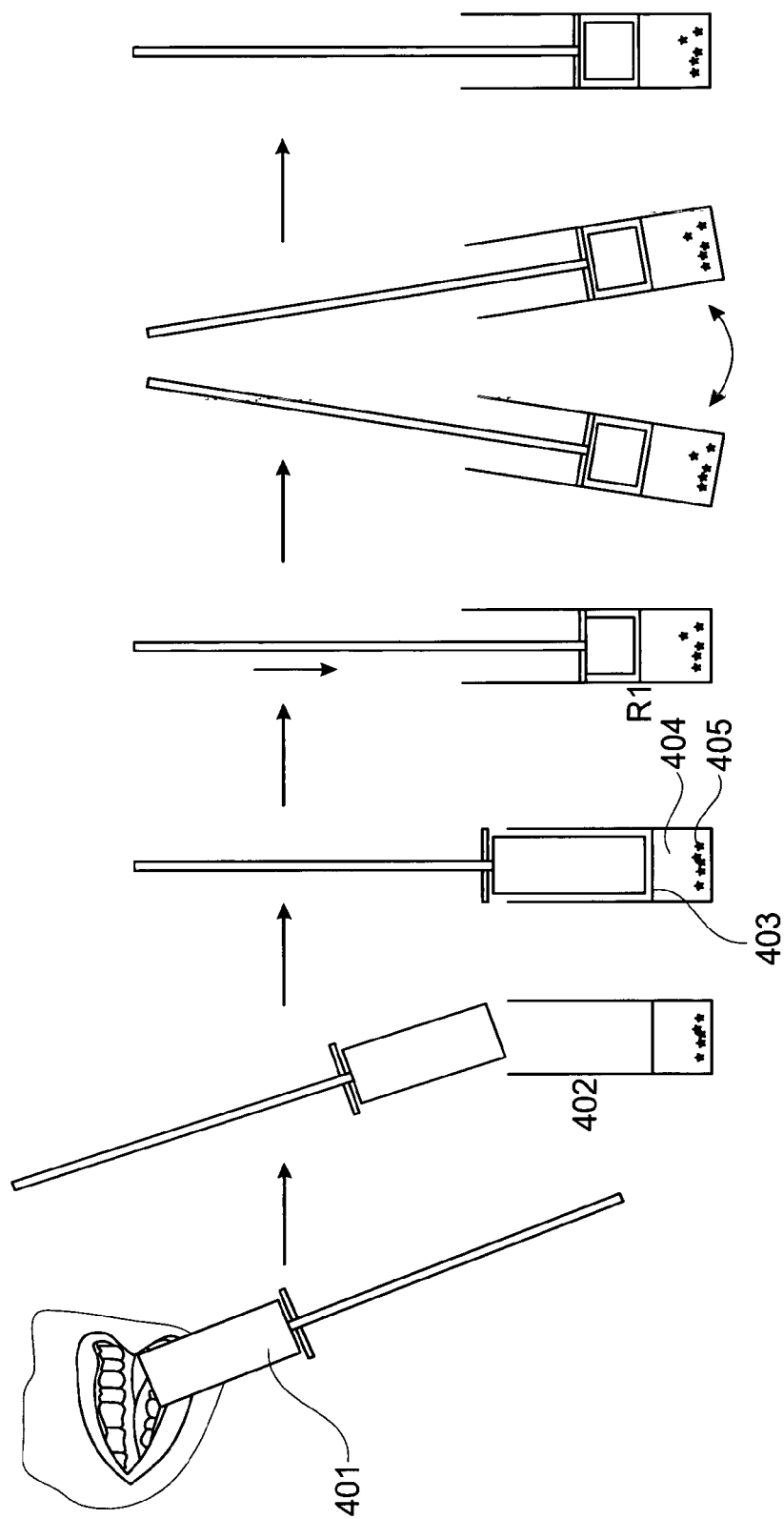
Figure 5:
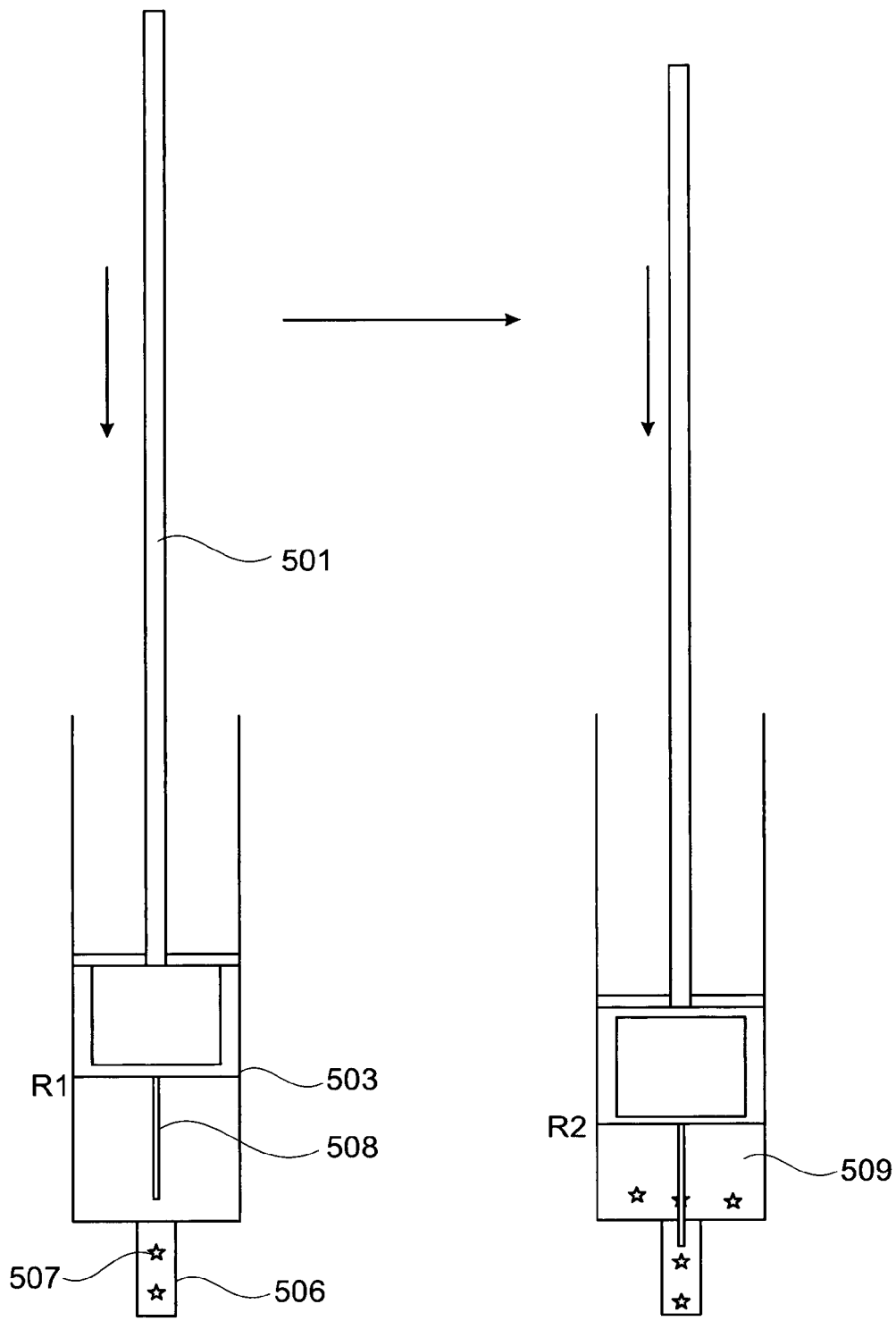
Figure 6:
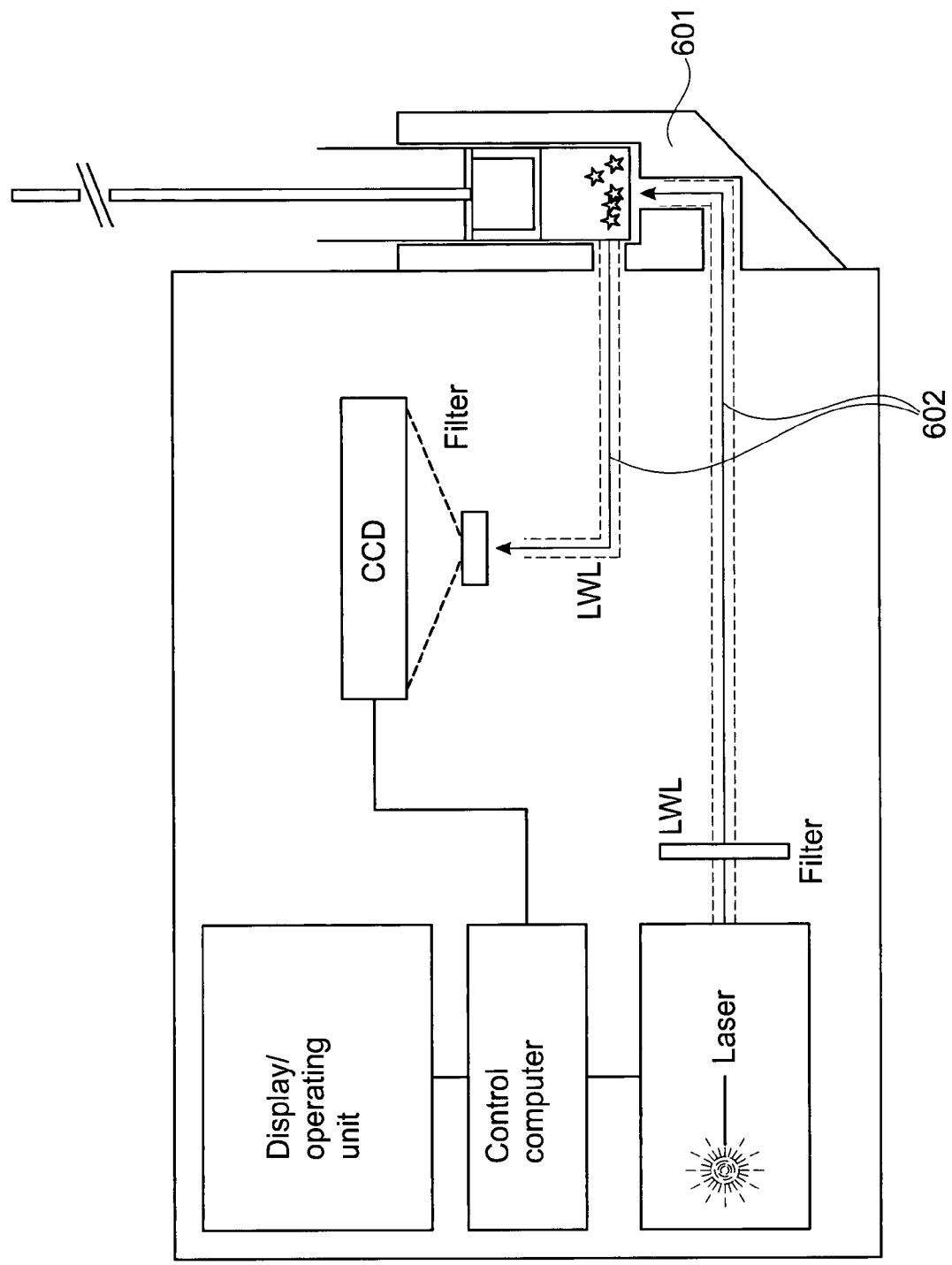
Figure 7A:
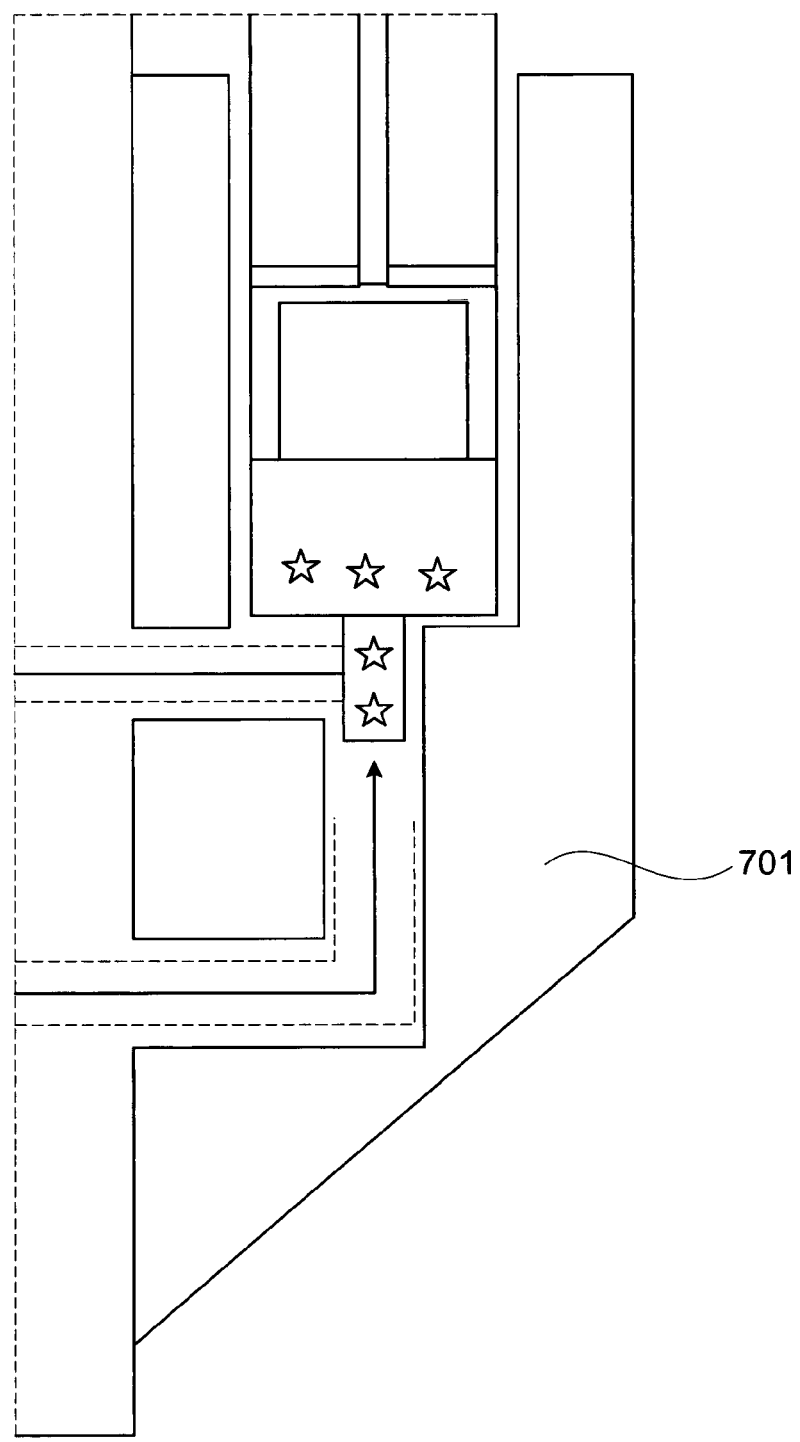
Figure 8A:
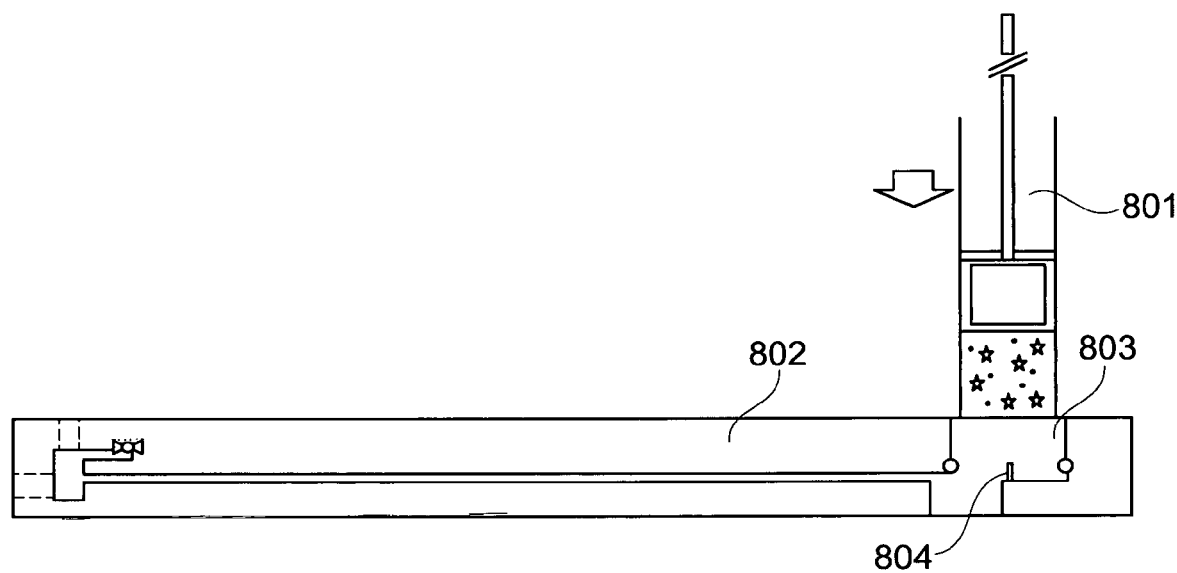
Figure 8B:
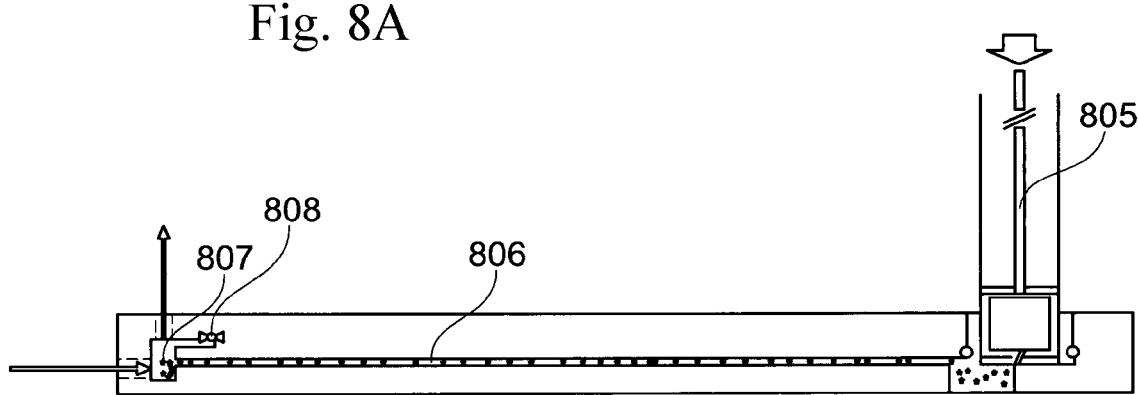
Figure 8C:
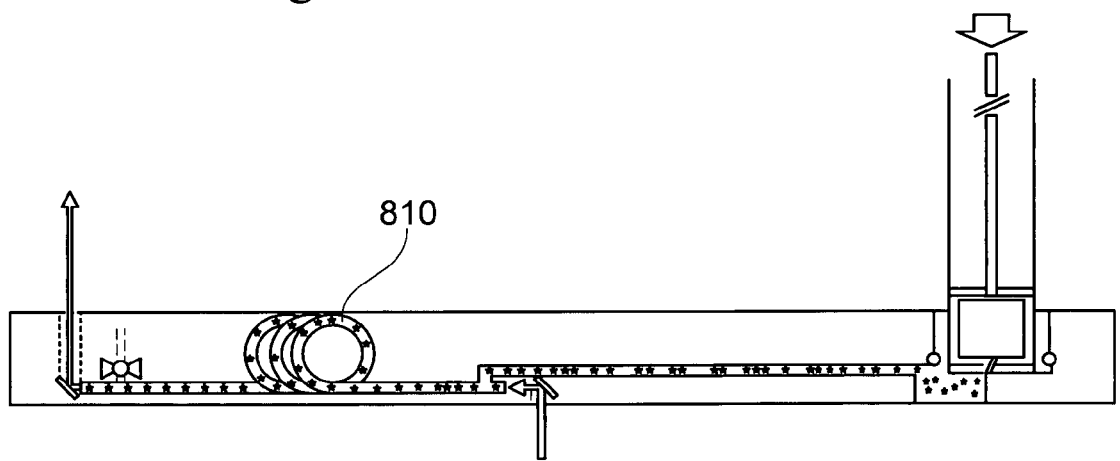
Figure 9A:
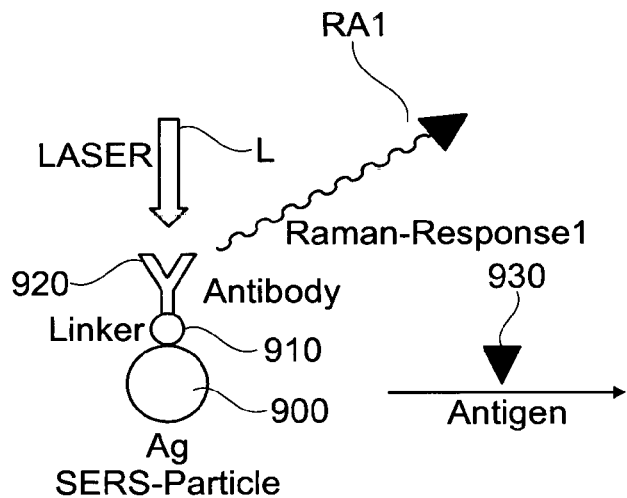

In the figures it is shown:

FIG. 1 a schematic basic structure of an example device according to the present invention for the determination of an analyte using SERS;

FIG. 2A a combination of a sampling device and a microfluidic analysis device before contacting with an eluent;

FIG. 2B a combination of a sampling device and a microfluidic analysis device after contacting with the eluent;

FIG. 3A a microfluidic device comprising a hollow core optical fiber before contacting with an eluent according to a further embodiment of the present invention;

FIG. 3B the microfluidic analysis device according to FIG. 3A after contacting with an eluent;

FIG. 4A, B, C a two-part sampling device with a part for taking up the sample including a sample matrix and SERS particles in a mixing container;

FIG. 5 introduction of a sampling device into an elution container with SERS reservoir serving as an analysis device;

FIG. 6 a schematic direct reading of the sampling device according to FIG. 4;

FIG. 7A, B, C a reading of the analysis device of FIG. 5;

FIG. 8A insertion of a two-part sampling device including a sample matrix and an elution container into a microfluidic analysis device;

FIG. 8B a filling of the microfluidic analysis device according to FIG. 8A;

FIG. 8C a microfluidic analysis device including a hollow core optical fiber;

FIG. 9A, B functionalization of the SERS-particles with anti-bodies; and

Figure 10:
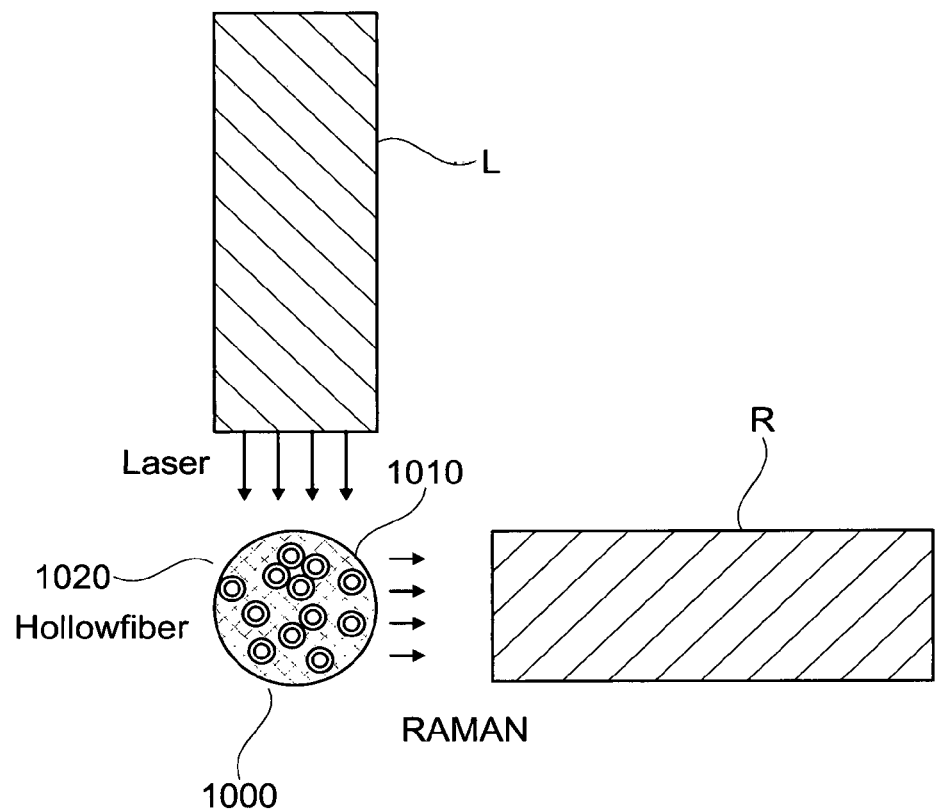

FIG. 10 further details in connection with an example embodiment comprising a hollow core optical fiber.

FIGURES

FIG. 1

Basic structure of a device according to the invention for the determination of an analyte using SERS comprises:

a housing of the analysis device 1, a sampling device 2, a microfluidic analysis device 3, a reservoir containing an eluent (separate region of the analysis device) 4, a laser 5, an optical fiber 5a, 5b (or any other optical guidance means or optical waveguide)

a filter 6, a filter 7, a CCD device 8, a control computer 9, and a display/operating unit 10.

The housing of the analysis device 1 is connected with the sampling device 2 and they also cover the microfluidic analyses device 3.

Moreover, the reservoir 4 is attached to the housing of the analysis device 1.

The laser 5 is optically connectable or connected (as shown in FIG. 1) with a specific optical coupling of the analysis device 1 and the laser beam excited by the laser 5 passes a filter 6 before entering the optical coupling of the analysis device 1.

The laser 5 is guided by means of optical waveguides 5a, 5b, wherein one optical waveguide 5a is provided for sending from the laser 5 to the microfluidic analysis device 3 and from the microfluidic analysis device 3 to the filter 7 by means of another optical waveguide 5b.

The control computer 9 is connected with the laser 5 and also connected with the display and operating unit 10. By means of the display and the operating unit 10 specific results are operating options may be displayed and also an user input can be done via the display or specific button, with which the control computer 9 can be operated.

By means of the CCD camera 8 the outcoming optical signal out of the analysis device 1 is routed via the filter 7 to the CCD camera 8.

The optical analysis of the CCD signal 8 is done via the control computer 9.

As a suitable laser module with a fiber coupled semiconductor laser (continuous wave (CW) with a wavelength of 785 nm (NIR) and a controllable laser power of up to 200 mW may be used. Such a laser is beneficial as it enables on the one hand a good fluorescence avoidance and a spectral sensitivity of the detector on the other hand.

Also, in a further embodiment a semi conductor laser in the UV-range may be used. As long as the wavelength is significantly below 300 nm, noise may be avoided by auto fluorescence radiation of the sample. Furthermore, the signal intensity of the Raman radiation is increased with reduced wavelength. Both effects lead to a better signal-to-noise ratio.

The wave guiding within the device is realized with multi model-optical waveguides.

Such an optical waveguide may have a quartz glass core and sheath and may be coated with a polymer protection sheath.

The core diameter is at least 300 μm, the numerical aperture is typically NA 0.22.

For coupling of the laser beam into the optical waveguide for example a spherical lens or a rod lens may be used or an arrangement of aspherical lenses.

The "inlet" filter 6 is used for preparation of the laser beam before coupling and sending into the sample. Unwanted wavelengths are removed by means of a band pass filter with narrow band width (background-removal).

The filtered laser signal is then focused with a lens arrangement into the measurement chamber of the test cassette as for example shown in FIG. 8B or into a further waveguide (for example FIG. 8C).

Within the analysis device 1 an optimized excitation radiation may be focused with a lens arrangement directly into the measurement chamber of the test cassette as shown in for example FIG. 2B and FIG. 7. For increasing the results of the Raman-scattered radiation, the measurement chamber may be reflective on the inside and/or have a concave shape.

In further embodiment, the laser radiation may be coupled by means of a optical hollow fiber. Here, coupling optics or passive reflectors and/or tilted mirrors may be used.

There may be an optical filter module for the Raman scattering.

Within the test cassette excited scattering may be guided by means of suitable optics to the receiving waveguide 5a of the reader. The optics may be part of the test cassette or also integrated in the analysis device or the reader.

The scattering may be guided by means with the receiving waveguide to the filter 7 and by means of e.g. a notch filter, the unwanted part of the Rayleigh scattering is filtered.

The detector module 8 is especially suitable for a wavelength range of 800-1100 nm.

There may be a slit mask for vignetting the radiation (ca. 10-20 μm slit width), a concave collimator-mirror, an optical diffraction grating and an optical assembly for focusing on the CCD element 8.

In a further embodiment the number of optical components may be reduced by using a cross-section converter instead of a slit mask and a concave blazed holographic grating.

The CCD array element may have a higher sensitivity in the NIR range and for example a resolution of 2048×64 pixels (for example Hamamatsu S11510-1106).

Alternatively, a so-called BT-CDD chip (back-thin) may be used to achieve a higher quantum efficiency.

For improving the signal-to-noise ratio further, the CCD element may be thermo-electrically cooled with a Peltier element.

The control unit 9, which is connected with the CCD element 8 digitalizes the signals from the CCD element 8 and processes an analysis result.

By means of a signal comparison with available target-spectra ("fingerprints") for the analytes of interest, a fast and specific analysis may be performed.

FIGS. 2A and B

A combination of sampling device and microfluidic analysis device before (FIG. 2A) and after (FIG. 2B) contacting with eluent, comprising
a sampling device 2;
microfluidic analysis device 3 containing a separate region 4, which comprises an eluent with SERS active nanoparticles dispersed therein,
microfluidic mixing path 12;
microfluidic valve 13 for allowing a balance of pressure;
detection chamber 14 (second region of the microfluidic analysis device).

FIG. 2A illustrates the introduction of a sampling device into a microfluidic analysis device. The sample matrix wetted with a saliva sample is pressed into a washing chamber of the microfluidic analysis device 3 and insulated on the side 11. By means of a subsequent manual compressing of a reservoir 4, the eluent contained therein is set free and a pumping effect for transporting such eluent through the channels 12 of the microfluidic analysis device is produced. A microfluidic valve 13 allows a balance of pressure. The eluent may contain SERS active particles (*). From this pumping effect, the sample matrix is flushed with the eluent and thus the sample/analyte is dissolved in the eluent and mixed while being transported through fluidic channels 12 to the detection chamber 14, i.e. the optical interface of the spectroscopic evaluation. The detection chamber may contain SERS active particles.

FIG. 2B shows the microfluidic analysis device after compression of the reservoir. The eluent now washes over the sample matrix. SERS active nanoparticles (*) are homogenously dispersed in the eluent in which the analyte is dissolved.

FIGS. 3A and B

Microfluidic analysis device comprising a hollow core optical fiber 15. The optical hollow fiber comprises a hollow core 16, a glass capillary 17 and optionally a casing 18. The capillary 17 can additionally contain on its inside surface a coating with SERS active nanoparticles 19. The coupling and uncoupling of the laser and Raman radiation, respectively, as illustrated in FIG. 3B is achieved by deflection mirrors 20 or a corresponding positioning of the optical fiber.

FIGS. 4A and 4B

Two-part sampling device with a part for taking up the sample including the sample matrix 401 and a mixing container 402. A saliva sample is taken up using the part including the sample matrix 401. Subsequently, the part including the sample matrix 401 is introduced into the mixing container 402 and manually compressed therein until it is in lock position R1. By this procedure, the saliva sample is sent through at least one sieve-like intermediate base and brought to a mixing zone 404 which contains dried SERS nanoparticles 405.

By subsequent manual shaking, the SERS particles are dispersed in the sample.

By mixing of the substances by manual shaking, a good dispersion of all substances may be achieved.

The mixing of the substances may be achieved by manual shaking of the whole analysis device. It may also be achieved by shaking the cassette.

The analysis device is then inserted in the receiving portion of the reading device as shown in FIG. 6 and FIG. 7.

Figure 7B:
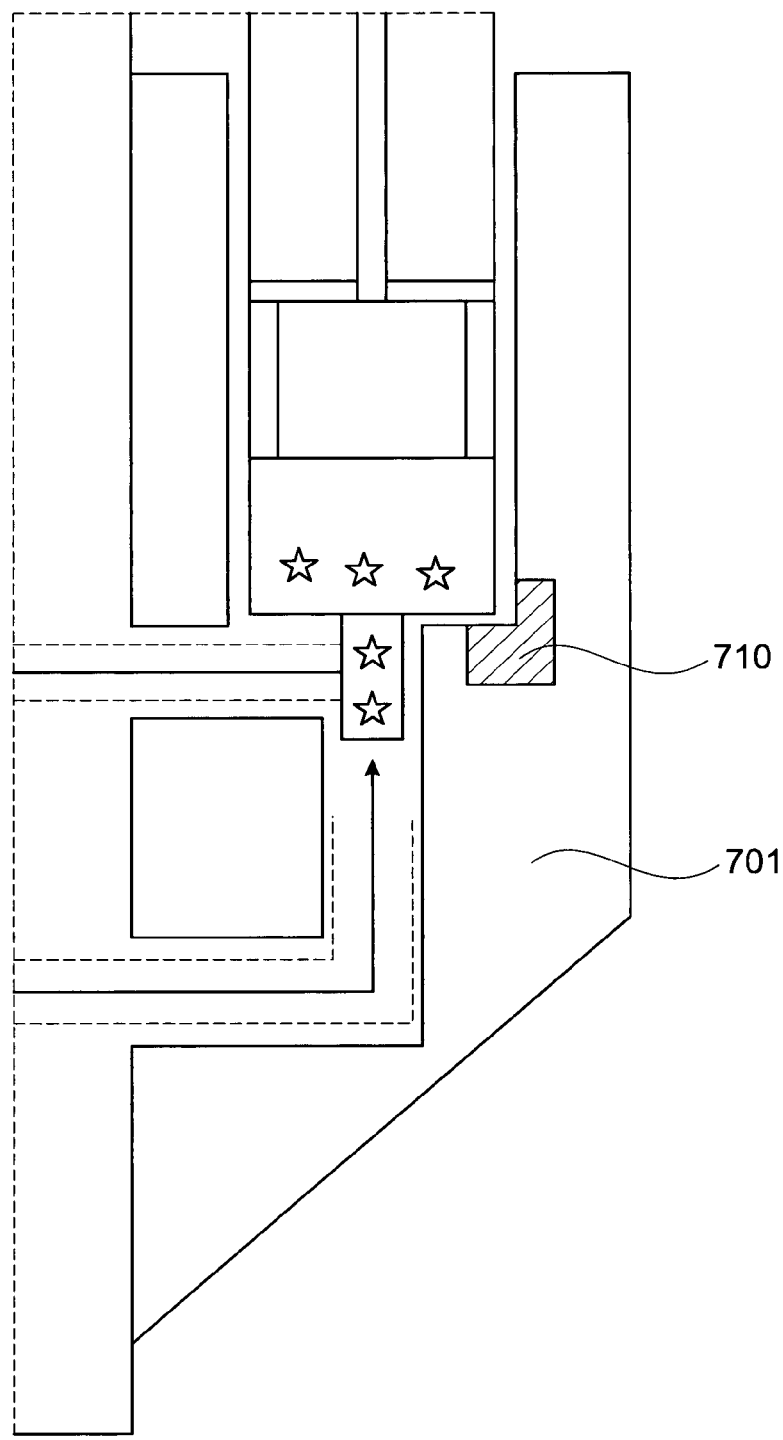
Figure 7C:
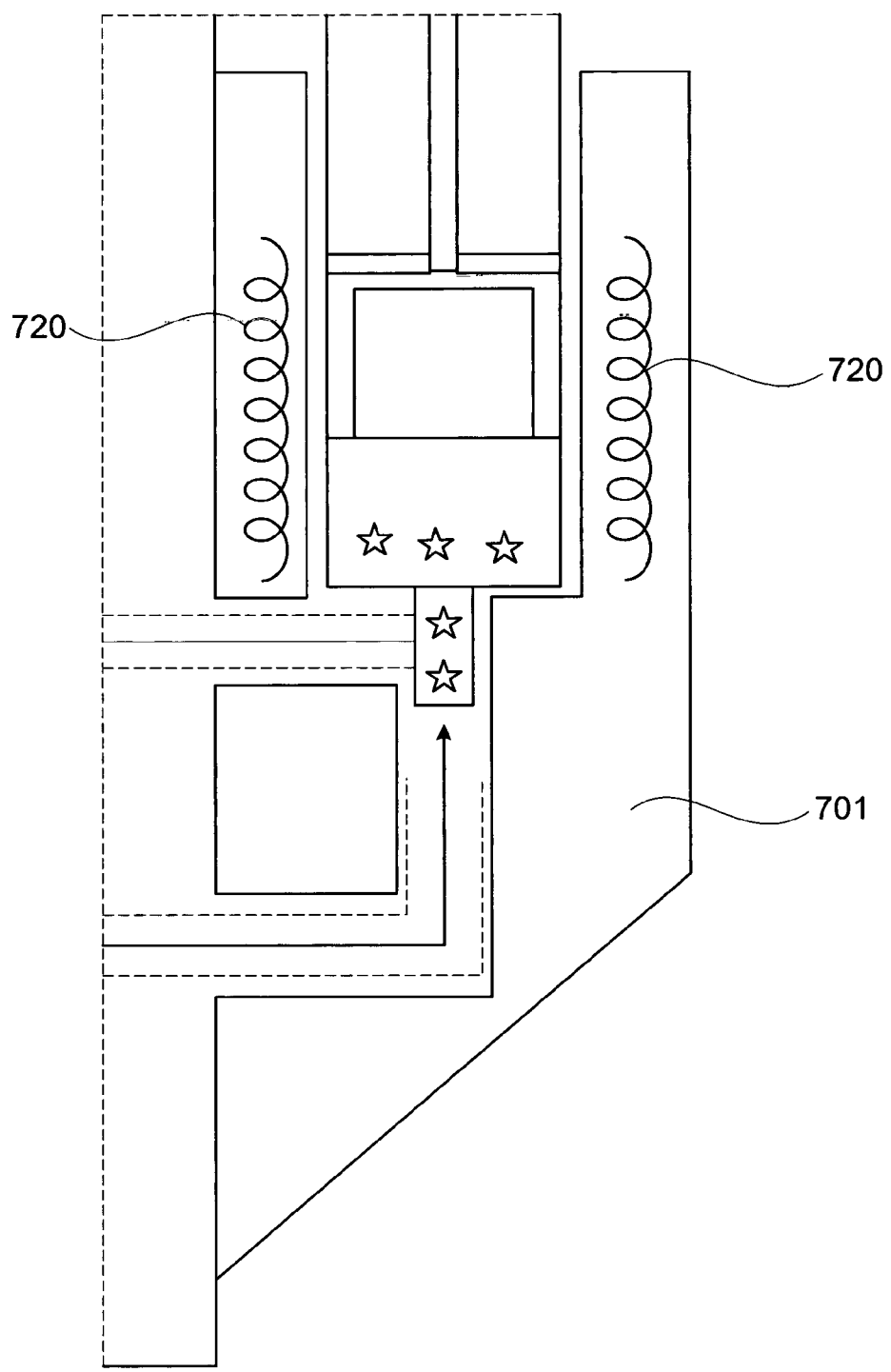

The receiving portion comprises a magnetic coil 720 as shown in FIG. 7C. It will provide a varying magnetic field, which will cause movement of the magnetic particles within the solution and thus cause a homogeneous mixing.

For reliable dispersing of dried SERS-particles or a coating of dried SERS-particles with a low amount of saliva, the following structure and procedure may be provided:

The extraction container may comprise a mixing zone 404, which comprises a soluble coating with SERS particles as further shown in FIG. 4B and FIG. 4C.

In the mixing zone there are freely moveable, magnetic particles or miniature mixing spheres or objects 406.

These mixing objects are excited by an external magnetic field 407, which can be arranged in the receiving portion of the reading device for a circular or elliptical movement within the mixing zone 404.

The detection area is equipped with inlet optics 409 and outlet optics 411.

A partition wall 410 is separating the mixing zone from the detection zone.

The partition wall 410 may comprise a reflective coating directed to the detection zone and thus may act as a mirror.

Furthermore, this partition wall 410 may be concave.

The function of the procedure shown in FIG. 4B, 4C is as follows:

The saliva, which has been collected with the sampling device 401 is transferred into the mixing chamber 404 by compressing it to position R1 (shown in FIG. 4C).

The sampling container 402 is then inserted into the receiving portion of the reading device.

Especially by means of the optical sensor 710 as shown in FIG. 7B, the correct positioning of the sampling container within the receiving portion is checked.

By means of magnetic excitation, the magnetic particles 406 in the mixing chamber 404 are brought into movement, which enhances the release of the SERS coating 405 and a mixing of the SERS particles with the saliva sample 403 brought into the mixing chamber 404.

By means of the laser radiation for excitation of the Raman effect by means of the optical waveguide 408 and the optical device 409, which may comprise an inlet lens, the laser radiation is led into the detection chamber 413.

The so generated scattering radiation is trapped with the optic module 411, which is here comprising a spherical lens.

By means of the optical module 411 the generated scattered radiation is coupled into the receiving optical waveguide 412.

FIG. 5

Introduction of a sampling device 501 into an elution container with SERS reservoir serving as an analysis device. The elution container includes a separate reservoir 506 that is filled with a liquid (the eluent) comprising SERS active particles 507 dispersed therein. In the left part of the figure, the sampling device 501 including a sample matrix soaked with a liquid sample is introduced into a first region of the elution container and manually compressed until it is in lock position R1 to release the liquid sample through a sieve-like intermediate base 503 into a mixing chamber 509 of the elution container. Upon further pressing the sampling device 501, the sieve-like intermediate base 503 is placed into lock position R2 as shown in the right part of the figure. The intermediate base contains a mandrel 508, which opens the reservoir 506 when in position R2. By subsequent manual shaking, the solution (eluent) contained in the reservoir 506 is thus mixed with the sample. Additionally, the solution (eluent) rinses the sample matrix and thus flushes out any remaining analyte.

FIG. 6: Direct Reading of the Sampling Device of FIG. 4

For the analysis, the sampling device of FIG. 4 is placed in a holder 601 of the reading device. Coupling and uncoupling of laser and Raman radiation are achieved by optical fibers 602.

FIG. 7: Reading of the Analysis Device of FIG. 5

The elution container of FIG. 5, serving as an analysis device, is placed in a holder 701 of the reading device. The reservoir includes a defined volume of eluate comprising the analyte-containing sample dissolved in the eluent with SERS active particles dispersed therein. Coupling and uncoupling of laser and Raman radiation are achieved by optical fibers.

FIG. 7B shows the reading of the analysis device as shown in FIG. 7, with an additional, optional detail.

While placing the elution container, serving as analysis device in the holder 701 of the reading device, this placement may be assisted by the analysis device and the respective geometries.

The container may be in the shape of a cassette, especially a disposable cassette.

There may be a guiding structure, which my allow insertion only in one possible way to create a so-called "foolproof" solution.

The opening of the receiving portion of the analysis device may be protected by means of an optical lid (not shown). By means of this optical lid, unwanted optical influence from the outside may be prevented.

To ensure a correct coupling an additional sensor 710 may be provided.

By means of the sensor 710 the correct positioning of the cassette within the holder 1 may be checked.

For a correct coupling of the laser beam it is important that the cassette has reached a defined end-position within the holder 1.

In the shown embodiment, this is realized by means of an optical sensor 710.

However, any other sensor like an electrical switch, a magnetic sensor, an electrical sensor or the like may be used.

In a possible further embodiment of the test cassette as shown in FIG. 4 and FIG. 5 the mixing of the minimal volumes of for example saliva with a SERS solution may be enhanced.

A mixing of saliva with the SERS solution is beneficial for the detection of the analytes.

For this reason, the receiving portion may be equipped with a magnetic coil 720 (cf. FIG. 7C).

By using magnetic microparticles or nanoparticles in the SERS-solution and a magnetic induced movement, a mixing effect may be achieved. Furthermore, by using the magnetic particles and the coil, information about the viscosity of the fluid can be obtained by the inverse effect: The particles still in movement will induce a voltage in the coil 720, wherein depending on the viscosity of the fluid, a voltage proportional to the residual movement of the magnetic particles can be measured. The higher the viscosity, the lower the residual particle movement, the lower induced voltage.

Furthermore, there may be optical collimators in any of the described embodiments which will allow an incoupling or outcoupling of the laser beam into the optical waveguides 5a, 5b (FIG. 1).

As a further point, SERS particles with identical characteristics are hard to reproduce. Therefore, a receiving portion may be equipped with a code reader to read out production-lot specific parameters from the test cassette, which will be inserted into the receiving portion of the holder 1. Such code readers may be for example RFID readers, barcode readers, QR-code readers or the like.

If there is no test cassette in the receiving portion then the receiving portion opening will be protected by means of a protection mechanism.

Such protection mechanism may be embodied with a spring activated mechanism and a sealing.

By this protection mechanism the intake of contaminations of any kind may be avoided.

FIG. 8A

Insertion of a two-part sampling device including a sample matrix and an elution container into a microfluidic analysis device. The sampling device 801 containing an eluate of the analyte with SERS active particles dispersed therein is placed in a sealed fitting 803 of the microfluidic analysis device 802. By means of a mandrel 804 provided in the analysis device, the base of the elution container is then opened at a predetermined breaking point.

FIG. 8B

Filling of the microfluidic analysis device: by further pressing of the sampling device 805, the eluate is transferred into the microfluidic analysis device, optimally mixed in mixing channels 806, and transported to the detection chamber 807. This chamber can be coated with SERS nanoparticles (*). A balance of pressure is achieved by a microfluidic valve 808.

FIG. 8C

Microfluidic analysis device including a hollow core optical fiber 810. The optical fiber can contain on its inside surface a SERS active coating, preferably with SERS active nanoparticles, whereby the Raman effect is additionally enhanced.

In any of the above described devices a kit may be used, wherein the eluent present and the sampling device and/or in the analysis device comprises SERS-active nanoparticles dispersion therein.

Especially, reference is made to the embodiments shown in FIG. 2A and FIG. 4.

The saliva sample, which shall be analyzed, is collected with an absorbent sampling device, especially a cotton bud, cotton swab or a Q-Tip or the like.

The extraction of the saliva from the sampling device may be enhanced and supported by means of elution.

The elution means or eluent is provided therefore in a reservoir of the sampling device or in the analysis device.

For freeing the eluent preferably a manual action is necessary, for example pressing on the reservoir and thereby braking a seal.

The movement of the eluent is shown in FIGS. 1, 2A, 4, 5 and 6.

The eluent may comprise substances for treating the saliva sample.

Moreover, the eluent may also comprise so-called SERS-nanoparticles.

In connection and depending on the analyses to be detected, the particles may be made out of specific metals, sizes and characteristics and may be also chosen depending on the kind of analysis and also combined together with each other.

Preferably, SERS-nanoparticles comprising gold or silver or being gold or silver may be used.

This kind of SERS-particles has been reported to provide a very good enhancement in connection with the technology of the present invention.

The particles may be spherical, which is however not mandatory.

If the diameter of the particle chosen below, the wavelength of the excitation radiation. Typically, then the diameter then is chosen within a range of 50 to 200 nm.

Moreover, the nanoparticles may be bound with linking molecules to specific antibodies. With this mechanism, specific target antigens (analytes) may be specifically trapped and detected.

For characterization of the SERS-activity of the solution, the solution may also comprise control analytes.

The eluent may also comprise magnetic particles.

By means of the control analytes the shelf-live of the SERS-particles and whether or not the particles are still working can be detected.

For example, the shelf-live of SERS-particles or SERS-substrates may be relatively short, for example it is reported that some SERS-particles only have a shelf-life of 60 days.

By using magnetic particles and by using these particles for a mixing of the all components of the eluent and the solution, agglomeration of the nanoparticles may be avoided and a good dispersion of all components of the eluent can be achieved this way.

As a general remark it shall be mentioned that the use of metallic SERS-nanoparticles may enhance the relatively weak Raman signals by the factor of $10^4$ up to $10^6$. This effect is primarily achieved by means of the excitation of the metallic surface plasmons, which are excited by the laser radiation.

Thus, an electromagnetic interaction with the analyte molecules is achieved and an enhancement is provided.

The molecules may be bound to the metal or in the close vicinity of the electromagnetic field of the nanoparticles.

A clustering of nanoparticles may also provide better signals by creating so-called "hot-spots".

At 780 nm excitation radiation especially dimers with a size of around 80 nm are of interest.

For the Raman signal enhancement especially size, shape and surface of the SERS-particles is important.

The reproducibility of these parameters, however, may be difficult, especially from production lot to production lot.

Consequently, it is therefore proposed in connection with this disclosure that a characterization of the SERS-activity by means of a control substance is done. Prior to the analyte detection itself, the Raman spectrum of the known reference substance is analyzed and detected and a self calibration is performed. By this, a good reproducibility of the detection may be guaranteed. Also, the accuracy of the overall system and process is significantly enhanced.

Also, by a possible functionalization of the SERS-particles with anti-bodies selective target analytes may be bound.

Figure 9B:
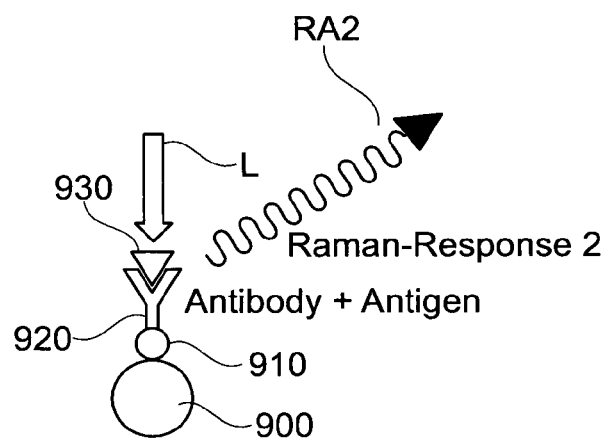

This is shown in FIGS. 9A and 9B.

In FIG. 9A a silver SERS-particle 900 is shown. Bound to the particle 900 a linker 910 and a anti-body 920 is bound to the linker 910.

An excitation with the laser L leads to a Raman signal or Raman response RA1.

When adding an antigen 930, which is then bound to the anti-body 920 as shown in FIG. 9B, the laser excitation leads to a Raman response RA2.

By this approach it becomes possible to detect very specifically different analytes and to adjust the SERS-solution to target analytes of interest.

FIG. 10 shows further details in connection with an example embodiment comprising a hollow core optical fiber 1000, having a hollow core 1005 and an wall 1020 with an coating 1010 on its inside wall.

In an embodiment, where the second region of the kit comprises a hollow-core optical fiber that may optionally be coated on its inside surface and that is configured to receive the analyte-containing sample in its hollow-core, the following points have been observed:

For a total reflection the refractive index of the analyte-sample-solution (aqueous solution ca. 1.33) must be bigger than the refractive index of the quartz glass wall 1020 (ca. 1.46).

To solve this specific aspect, substances that increase the refractive index, like glycerin paraffine oil or formazine may be added to the solution.

In such a connection, the structure may be realized as follows (but not limited to this example):

The test cassette may comprise a receiving portion with a seal for a wiper (see also FIG. 2A, reference no. 11 or for the sampling device (cf. FIG. 8A, reference no. 803).

The eluent solution is either in the reservoir of the test cassette likewise the embodiment shown in FIG. 2A, reference no. 4, or in the mixing chamber of the sampling device according to the embodiment shown in FIG. 8a.

In both cases the eluent provided in the reservoir may contain SERS-nanoparticles or SERS-clusters.

In the embodiment shown in FIG. 10 a quartz glass fiber with a hollow-core is used.

This fiber serves as microfluidic analysis chamber for the analyte solution but also as an optical waveguide for the incoming excitation laser radiation and the Raman radiation.

For the desired total reflection the wall must have a lower refractive index than the filled core.

At a refractive index of 1.46 for quartz glass the aqueous solution in the core is brought by means of additives like glycerin or paraffin oil or formazine to a refractive index of more than 1.46. Alternatively, a polymer fiber may be used with a refractive index of lower than 1.33, for example Teflon-AF.

It is also possible that a hollow-core fiber is used with a second sheath (see also FIG. 3A, number 18), which uses a refractive index that is lower than the refractive index of the first sheath 17.

Alternatively, a microstructured photonic crystal fiber may be used, which guides light not on the principle of inner total refraction but on the principle of photonic crystallic fibers/band gap fibers (PCF).

In a further variant, especially as shown in FIG. 10, the fiber for the laser radiation and the receiving optical fiber are arranged perpendicular to a hollow fiber filled with analytes.

The sheath of the hollow fiber works as an optical resonator.

The SERS-solution close to the hollow fiber walls is then excited to Raman radiation.

The optical module in the test cassette serves for condensing the excitation laser in the optical waveguide.

This module may comprise a focus lens, a reflection mirror and a semi-permeable mirror.

The latter may also be used for reflection of the scattered radiation within the hollow fiber and thus may serve as an enhancement element.

The length of the optical waveguide may be adapted to the volume of eluent and analyte, so that at a minimal allowable filling of the hollow-core, the hollow-core is completely filled. The hollow fiber may comprise on its inner walls SERS-active coatings.

At the end of the hollow fiber a spill over reservoir may be provided and also a water tight but air permeable seal for pressure equalization.

The function may be described as follows:

After taking a sample (e.g. of saliva) the wiper or the sampling device is inserted into the test cassette.

Depending on the sampling device mechanism the eluent is freed and mixed with the saliva sample.

By manually activating the reservoir or the sample device the solution is fed into the hollow fiber.

A potential overrun is taken up with the waste reservoir and if a pressure equalization is needed, then the semi-permeable membrane, which is water-tight but air permeable will provide the pressure equalization.

The laser excitation is focused either in or directed onto the hollow fiber and will generate the specific Raman scattering.

This specific Raman scattering will then be focused with the specific optic elements (cf. see above in the already described embodiments) into the receiving optical waveguide of the analysis device and will then be processed by means of e.g. the controller 9 and the CCD device 8.

The invention claimed is:

1. A kit for determining an analyte in a sample comprising:
   (a) a sampling device configured for taking up a sample containing an analyte, wherein the sampling device comprises a sample matrix; and
   (b) an analysis device, comprising:
      a first region which is configured for introducing the sampling device; and
      a second region which is configured for detecting the presence and/or amount of the analyte in said sample via surface enhanced Raman spectroscopy, wherein said regions are interconnected by at least one processing stage which is located downstream from the sample matrix with respect to an intended flow direction of a fluid and which processing stage makes it possible to process the fluid which contains an analyte eluted from the sample matrix while the fluid and the analyte contained by the fluid are passed from the first region to the second region within the analysis device.

2. The kit of claim 1, wherein the sampling device comprises a volume indicator.

3. The kit of claim 2, wherein the sample matrix of the sampling device comprises an absorptive material configured to absorb the analyte-containing sample and to release it upon contact with an eluent and/or mechanical compression.

4. The kit of claim 1, wherein the sampling device comprises at least two separate parts, wherein the first part comprises the sample matrix and the second part comprises an eluent for eluting the analyte from the sample matrix.

5. The kit of claim 1, wherein the analysis device comprises a microfluidic structure.

6. The kit of claim 1, wherein the second region comprises a hollow-core optical fiber.

7. The kit of claim 6, wherein the hollow-core optical fiber is coated on its inside surface with a SERS-active coating, the coating comprising SERS-active nanoparticles.

8. The kit of claim 6, wherein the hollow-core optical fiber is coated on its inside surfaces, and wherein the second region is configured to receive the analyte-containing sample in a hollow core of the hollow-core optical fiber.

9. The kit of claim 1, further comprising: a radiation source for generating monochromatic light;
   a detector for detecting inelastically scattered radiation; and
   optics for directing the radiation.

10. The kit of claim 9, wherein the radiation source includes laser radiation.

11. The kit of claim 1, wherein the analysis device further comprises a housing, wherein at least one of the sampling device and the analysis device comprises an eluent and at least one of the sampling device and the analysis device comprises SERS-active particles.

12. The kit of claim 11, wherein the eluent present in the sampling device and/or in the analysis device comprises SERS-active nanoparticles dispersed therein.

13. The kit of claim 11, wherein the second region comprises SERS-active nanoparticles, including dry SERS-active nanoparticles or a dispersion of SERS-active nanoparticles.

14. A method for detecting an analyte in a sample, comprising:
   (a) receiving a sample containing an analyte via a sampling device comprising a sample matrix and an eluent for eluting the analyte from the sample matrix;
   (b) introducing the sampling device into an analysis device, comprising at least a first and a second region, wherein the first region is configured for introducing the sampling device and the second region is configured for detecting the analyte in said solution;
   (c) transferring the analyte in a fluid from the first region via at least one processing stage which processing stage is located downstream from the sample matrix with respect to a flow direction of the fluid and in which processing stage the fluid and/or the analyte transferred in the fluid are processed while the fluid and the analyte transferred in the fluid are passed to the second region of the analysis device; and
   (d) determining the presence or/and amount of the analyte in the second region via surface enhanced Raman spectroscopy (SERS).

15. The method of claim 14, wherein the sample matrix of the sampling device comprises an absorptive material configured to absorb the analyte-containing sample and to release it upon contact with an eluent and the analysis device comprises a microfluidic structure.

16. The method of claim 14, wherein the analyte comprises one or more of cannabis, synthetic cannabinoids, ketamines, cocaine, heroin, methadone, methamphetamines, and a prescriptive drug.

17. The method of claim 14, wherein the sample comprises sweat, saliva, urine, or blood.

18. The method of claim 14, wherein the sample volume is between 30 µl to 150 µl.

19. The method of claim 14, wherein the eluent present in the sampling device and/or in the analysis device comprises SERS-active nanoparticles dispersed therein.

20. The method of claim 14, wherein the second region of the analysis comprises a hollow-core optical fiber coated on its inside surfaces with a SERS-active coating, and that is configured to receive the analyte-containing sample in its hollow core.

* * * * *